(12) United States Patent
Yang et al.

(10) Patent No.: US 12,097,048 B2
(45) Date of Patent: Sep. 24, 2024

(54) RADIOTHERAPY TREATMENT TABLE AND SYSTEMS AND METHODS USING THE SAME

(71) Applicant: SHANGHAI UNITED IMAGING HEALTHCARE CO., LTD., Shanghai (CN)

(72) Inventors: Hongcheng Yang, Shanghai (CN); Supratik Bose, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 945 days.

(21) Appl. No.: 17/117,154

(22) Filed: Dec. 10, 2020

(65) Prior Publication Data

US 2021/0177357 A1    Jun. 17, 2021

Related U.S. Application Data

(63) Continuation of application No. PCT/CN2019/124645, filed on Dec. 11, 2019.

(51) Int. Cl.
*A61B 5/00* (2006.01)
*A61B 5/055* (2006.01)
(Continued)

(52) U.S. Cl.
CPC ............ *A61B 5/704* (2013.01); *A61B 5/0036* (2018.08); *A61B 5/055* (2013.01); *A61B 5/706* (2013.01);
(Continued)

(58) Field of Classification Search
CPC ....... A61B 5/704; A61B 5/706; A61B 6/0407; A61B 6/0492; A61B 5/0036; A61B 6/582; A61B 5/0037; A61N 5/1049
See application file for complete search history.

(56) References Cited

U.S. PATENT DOCUMENTS

| 2004/0133980 A1 | 7/2004 | Coppens et al. |
| 2008/0031414 A1 | 2/2008 | Coppens |

(Continued)

FOREIGN PATENT DOCUMENTS

| CN | 2902196 Y | 5/2007 |
| CN | 201006193 Y | 1/2008 |

(Continued)

OTHER PUBLICATIONS

JP-11290293-A (Year: 1999).*

(Continued)

*Primary Examiner* — Joel Lamprecht
*Assistant Examiner* — Nyrobi Celestine
(74) *Attorney, Agent, or Firm* — METIS IP LLC

(57) ABSTRACT

A radiotherapy system is provided. The radiotherapy system may include a treatment component, an imaging component, and a table being movable between the treatment component and the imaging component along a first direction in a first coordinate system. The table may have a plurality of cross sections perpendicular to the first direction. The table may include a positioning line that extends along the first direction and have a positioning feature. The positioning feature may have a plurality of feature values. Each feature value may correspond to one of the plurality of cross sections.

19 Claims, 8 Drawing Sheets

(51) Int. Cl.
*A61B 6/04* (2006.01)
*A61B 6/58* (2024.01)
(52) U.S. Cl.
CPC .......... *A61B 6/0407* (2013.01); *A61B 6/0492* (2013.01); *A61B 6/582* (2013.01)

(56) References Cited

U.S. PATENT DOCUMENTS

| | | | |
|---|---|---|---|
| 2008/0123924 A1 | 5/2008 | Nabatame et al. | |
| 2008/0250565 A1 | 10/2008 | Timmerman et al. | |
| 2012/0316425 A1* | 12/2012 | Raleigh | A61N 5/1049 600/407 |
| 2013/0267830 A1 | 10/2013 | Ojha et al. | |
| 2014/0155736 A1* | 6/2014 | Vaidya | A61B 5/704 600/407 |
| 2016/0067525 A1* | 3/2016 | Bouchet | A61N 5/1069 600/1 |
| 2017/0049529 A1 | 2/2017 | Hannemann et al. | |
| 2017/0065233 A1* | 3/2017 | Yang | A61B 6/542 |
| 2018/0280223 A1* | 10/2018 | Hiratsuka | A61G 13/101 |
| 2019/0030366 A1* | 1/2019 | Maltz | A61B 5/0536 |
| 2019/0201717 A1 | 7/2019 | Shangguan et al. | |
| 2021/0346720 A1* | 11/2021 | Zhao | A61B 5/704 |

FOREIGN PATENT DOCUMENTS

| | | | |
|---|---|---|---|
| CN | 103054607 A | | 4/2013 |
| CN | 105078501 A | * | 11/2015 |
| CN | 108937987 A | | 12/2018 |
| CN | 109663223 A | | 4/2019 |
| CN | 110038233 A | * | 7/2019 |
| DE | 102006036575 A1 | | 2/2008 |
| JP | H1076020 A | | 3/1998 |
| JP | 11290293 A | * | 10/1999 |
| JP | H11290293 A | | 10/1999 |
| JP | 2002126106 A | * | 5/2002 |

OTHER PUBLICATIONS

JP-2002126106-A (Year: 2002).*
CN-110038233-A (Year: 2019).*
CN-105078501-A (Year: 2015).*
International Search Report in PCT/CN2019/124645 mailed on Aug. 31, 2020, 4 Pages.
Written Opinion in PCT/CN2019/124645 mailed on Aug. 31, 2020, 4 Pages.
The Extended European Search Report in European Application No. 19955565.7 mailed on Nov. 7, 2022, 9 pages.

* cited by examiner

700

701 — Actuating a table to move a subject from a first position with respect to a treatment component to a second position with respect to an imaging component, the table including a positioning line that has a positioning feature 702 — Acquiring a first image including the subject and at least a portion of the positioning line using the imaging component, the subject being located at the second position during the acquisition of the first image 703 — Determining a relative position of the second position to the first position based on the first image and the positioning feature of the positioning line 704 — Obtaining a second image of the subject, the second image being captured prior to the first image 705 — Registering the first image with the second image based on the relative position of the second position to the first position

```
801: Determining a third position of a first cross section of a table in a first coordinate system, the first cross section passing through an isocenter of a treatment component when a subject locates at a first position 802: Determining a feature value of a positioning feature corresponding to the first cross section of the table 803: Identifying, in a first image, a second cross section of the table that matches the first cross section based on the feature value of the positioning feature corresponding to the first cross section 804: Determining a fourth position of the second cross section in the first coordinate system 805: Determining a relative position of the second position to the first position based on the third position and the fourth position
```

FIG. 8

RADIOTHERAPY TREATMENT TABLE AND SYSTEMS AND METHODS USING THE SAME

CROSS-REFERENCE TO RELATED APPLICATIONS

This application is a continuation of International Patent Application No. PCT/CN2019/124645, filed on Dec. 11, 2019, which designates the United States of America, the contents of which are hereby incorporated by reference in their entirety.

TECHNICAL FIELD

The present disclosure generally relates to systems and methods for radiotherapy (RT), and more particularly, to a treatment table with a positioning line.

BACKGROUND

Radiotherapy is widely used in clinical treatment for cancers and other conditions. Conventionally, before a radiotherapy treatment on a cancer patient, a second image (e.g., a computed tomography (CT) image, a magnetic resonance imaging (MRI) image) of the cancer patient may be acquired using an imaging device. A treatment plan for the cancer patient may be made based on the second image. The treatment plan may be delivered to the patient during several treatment fractions, spreading over a treatment period of multiple days (e.g., 2 to 5 weeks). However, during the treatment period, an anatomical change (e.g., weight loss, growth, shrinkage, or disappearance of a tumor, the appearance of a new tumor, etc.) may take place within the body of the patient. The size and/or position of a certain organ may change between the time of planning and the time of one treatment fraction. Accordingly, before or during a current treatment fraction, a first image of the patient may be acquired and an anatomical change within the patient may be determined by registering the second image and the first image.

Normally, in the acquisition of the first image, the patient may be moved from a first position to a second position via a table and imaged at the second position. The second image and the first image may be registered to a common coordinate system to determine the anatomical change. In some occasions, due to operation error of the table, an actual moving path (e.g., a moving distance and/or a moving direction) of the table may be different from a planned moving path. The actual moving path of the table may need to be determined and taken into consideration in the registration. Thus, it may be desirable to develop effective devices, systems, and methods for tracking the movement of the table.

SUMMARY

According to one aspect of the present disclosure, a radiotherapy system is provided. The radiotherapy system may include a treatment component, an imaging component, and a table being movable between the treatment component and the imaging component along a first direction in a first coordinate system. The table may have a plurality of cross sections perpendicular to the first direction. The table may include a positioning line that extends along the first direction and have a positioning feature. The positioning feature may have a plurality of feature values. Each feature value may correspond to one of the plurality of cross sections.

In some embodiments, the system may further include at least one storage device storing a set of instructions for positioning in radiotherapy treatment, and at least one processor configured to communicate with the at least one storage device. When executing the instructions, the at least one processor may be configured to direct the system to perform the following operations. The at least one processor may be configured to direct the system to actuate the table to move a subject from a first position with respect to the treatment component to a second position with respect to the imaging component, and acquire a first image including the subject and at least one a portion of the positioning line using the imaging component. The subject may be located at the second position during the acquisition of the first image. The at least one processor may further be configured to direct the system to determine a relative position of the second position to the first position based on the first image and the positioning feature of the positioning line.

In some embodiments, to determine a relative position of the second position to the first position, the at least one processor may be configured to direct the system to determine a third position of a first cross section of the table in the first coordinate system. The first cross section may pass through an isocenter of the treatment component when the subject locates at the first position. The at least one processor may also be configured to direct the system to determine a feature value of the positioning feature corresponding to the first cross section of the table, and identify a second cross section of the table in the first image that matches the first cross section based on the feature value of the positioning feature corresponding to the first cross section. The at least one processor may further be configured to direct the system to determine a fourth position of the second cross section in the first coordinate system, and determine the relative position of the second position to the first position based on the third position and the fourth position.

In some embodiments, the third position of the first cross section may include a first coordinate of the first cross section along the first direction, and the fourth position of the second cross section may include a second coordinate of the second cross section along the first direction. The relative position may include a first distance between the second position and the first position along the first direction. To determine a relative position of the second position to the first position, the at least one processor may be configured to direct the system to determine the first distance based on the first coordinate and the second coordinate.

In some embodiments, the third position of the first cross section may include a third coordinate of at least one point of the positioning line at the first cross section along a second direction, and the fourth position of the second cross section may include a fourth coordinate of at least one point of the positioning line at the second cross section along the second direction. The second direction may be parallel with a surface of the table on which the subject lies and perpendicular to the first direction. The relative position may include a second distance between the second position and the first position along the second direction. To determine the relative position of the second position to the first position, the at least one processor may be further configured to direct the system to determine the second distance based on the third coordinate and the fourth coordinate.

In some embodiments, to determine a feature value of the positioning feature corresponding to the first cross section of the table, the at least one processor may be configured to direct the system to obtain a lookup table recording feature values of the positioning feature corresponding to the plurality of cross sections of the table. The at least one processor may be further configured to direct the system to determine the feature value of the positioning feature corresponding to the first cross section of the table based on the third position of the first cross section by looking up the lookup table.

In some embodiments, the at least one processor may be further configured to direct the system to obtain a second image of the subject, and register the first image and the second image with each other based on the relative position of the second position to the first position. The second image may be captured prior to the first image.

In some embodiments, the positioning line may have an N-shape. A cross section of the plurality of cross sections may have a first point, a second point, and a third point of the positioning line. The second point may be located between the first point and the third point. The positioning feature may include at least one of a third distance between the first point and the second point, a fourth distance between the second point and the third point, a ratio of the third distance to the fourth distance, a ratio of the fourth distance to the third distance, or a difference between the third distance and the fourth distance.

In some embodiments, the positioning line may have at least one of an A-shape, an S-shape, a V-shape, or a W-shape.

In some embodiments, a density of the positioning line may be different from a density of the table.

In some embodiments, the imaging component may be a computed tomography device, and the positioning line may include at least one of copper, iron, or aluminum.

In some embodiments, the imaging component may be a magnetic resonance imaging device, and the positioning line may include oil.

According to another aspect of the present disclosure, a method for patient positioning using a radiotherapy system is provided. The radiotherapy system may include a treatment component, an imaging component, and a table being movable between the treatment component and the imaging component along a first direction in a first coordinate system. The table may have a plurality of cross sections perpendicular to the first direction. The table may include a positioning line that extends along the first direction and have a positioning feature. The positioning feature may have a plurality of feature values. Each feature value may correspond to one of the plurality of cross sections.

In some embodiment, the method may include actuating the table to move a subject from a first position with respect to the treatment component to a second position with respect to the imaging component. The method may also include acquiring a first image including the subject and at least one a portion of the positioning line using the imaging component. The subject may be located at the second position during the acquisition of the first image. The method may further include determining a relative position of the second position to the first position based on the first image and the positioning feature of the positioning line.

According to another aspect of the present disclosure, a non-transitory computer-readable storage medium including instructions for positioning in radiotherapy treatment using a radiotherapy system is provided. The radiotherapy system may include a treatment component, an imaging component, and a table being movable between the treatment component and the imaging component along a first direction in a first coordinate system. The table may have a plurality of cross sections perpendicular to the first direction. The table may include a positioning line that extends along the first direction and have a positioning feature. The positioning feature may have a plurality of feature values. Each feature value may correspond to one of the plurality of cross sections.

In some embodiments, when the instructions are accessed by at least one processor, the set of instructions direct the at least one processor to effectuate a method, and the method comprising actuating the table to move a subject from a first position with respect to the treatment component to a second position with respect to the imaging component. The method may also include acquiring a first image including the subject and at least one a portion of the positioning line using the imaging component. The subject may be located at the second position during the acquisition of the first image. The method may further include determining a relative position of the second position to the first position based on the first image and the positioning feature of the positioning line.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings.

The drawings are not to scale. These embodiments are non-limiting exemplary embodiments, in which like reference numerals represent similar structures throughout the several views of the drawings, and wherein:

FIG. 7 is a flowchart illustrating an exemplary process for registering a second image with a first image according to some embodiments of the present disclosure; and FIG. 8 is a flowchart illustrating an exemplary process for determining a relative position of a second position to a first position according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
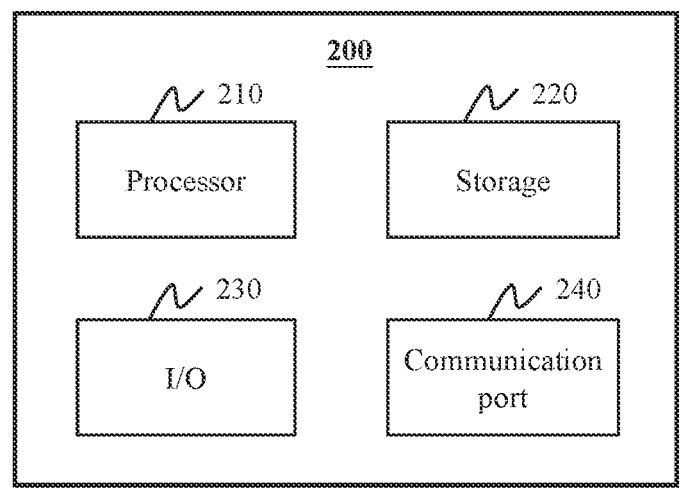
FIG. 2 is a schematic diagram illustrating an exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging and/or treatment, such as for disease diagnosis, treatment or research purposes. In some embodiments, the systems may include an RT system, a computed tomography (CT) system, an emission computed tomography (ECT) system, an X-ray photography system, a positron emission tomography (PET) system, or the like, or any combination thereof. For illustration purposes, the disclosure describes systems and methods for radiotherapy.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a second image, or a first image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

An aspect of the present disclosure relates to an RT system. The RT system may include a treatment component, an imaging component, and a table being movable between the treatment component and the imaging component along a first direction in a first coordinate system. The table may have a plurality of cross sections perpendicular to the first direction. The table may also include a positioning line that extends along the first direction and has a positioning feature. The positioning feature may have a plurality of feature values, each of which may correspond to one of the plurality of cross sections.

In some embodiments, the positioning line with the positioning feature may be used to track the movement of the table. For example, before a treatment fraction, a subject may be placed on the table and moved from a first position with respect to the treatment component to a second position with respect to the imaging component for acquiring a first image at the second position. The positioning line may be used in determining a relative position of the second position to the first position. Optionally, the first image and a second image of the subject may be registered with respect to a common coordinate system based on the relative position of the second position to the first position. By using a positioning line with a positioning feature, the relative position of the second position to the first position may be determined without placing one or more markers (e.g., metal marks) on the subject and/or implanting one or more markers into the subject. This may improve the efficiency and convenience of the process by, e.g., saving the marking and/or implantation procedure. In addition, determining the actual relative position of the second position to the first position may improve the precision of registration and treatment delivery, and/or reducing or avoiding unnecessary damages to the subject caused by inaccurate radiation delivery to the subject.

Figure 1:
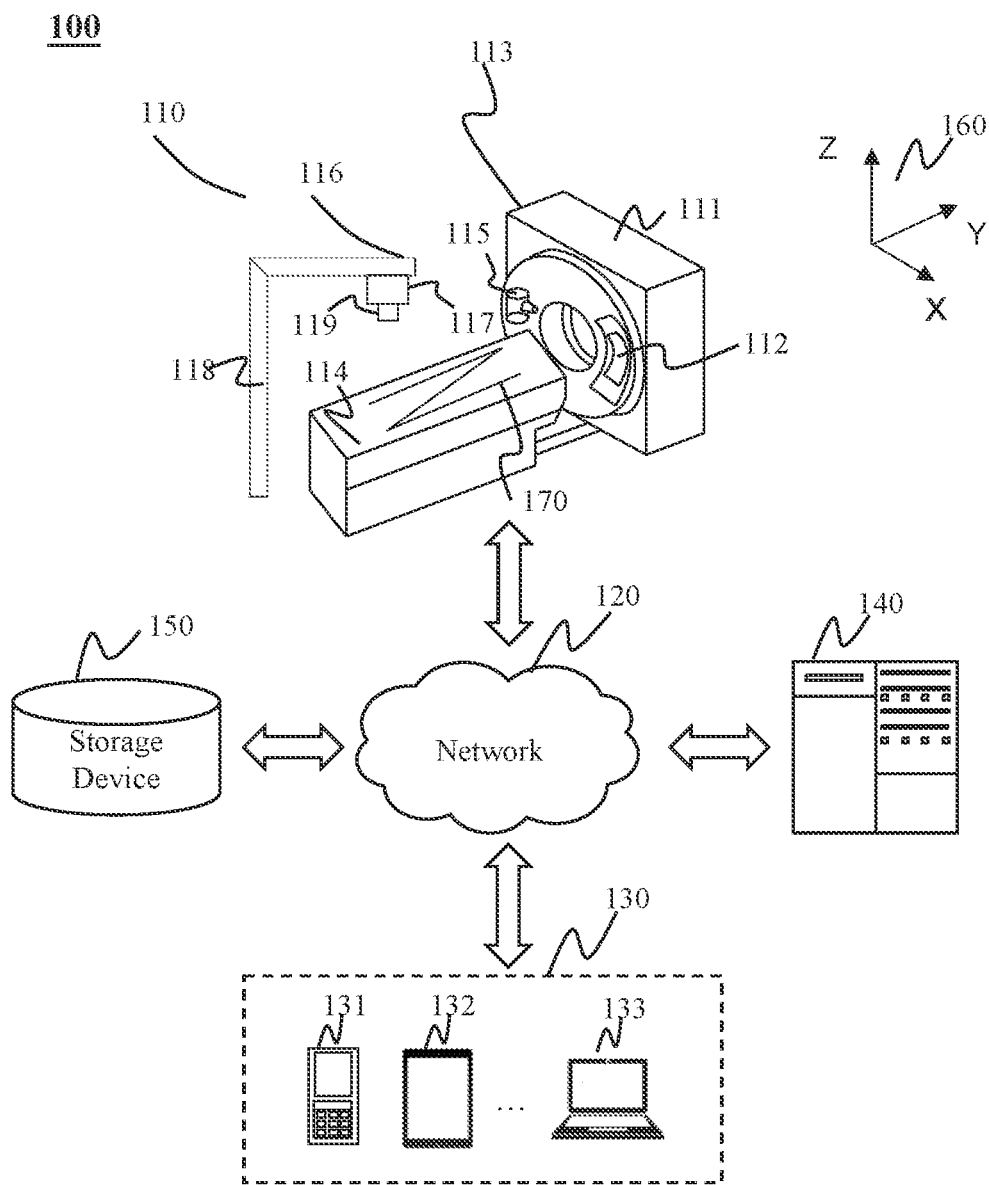
FIG. 1 is a schematic diagram illustrating an exemplary RT system according to some embodiments of the present disclosure.

FIG. 1 is a schematic diagram illustrating an exemplary RT system 100 according to some embodiments of the present disclosure. The RT system 100 may include a radiation delivery device 110, a network 120, a terminal 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely byway of example, the radiation delivery device 110 may be connected to the processing device 140 through the network 120 or directly. As a further example, the storage device 150 may be connected to the processing device 140 through the network 120 or directly.

The radiation delivery device 110 may include an imaging component 113, a treatment component 116, a table 114, or the like. The imaging component 113 may be configured to acquire an image of a subject prior to a radiotherapy treatment, during the radiotherapy treatment, and/or after the radiotherapy treatment. The subject may include any biological subject (e.g., a human being, an animal, a plant, or a portion thereof) and/or a non-biological subject (e.g., a phantom). For example, the imaging component may include a computed tomography (CT) device (e.g., a cone beam computed tomography (CBCT) device, a fan-beam computed tomography (FBCT) device), an ultrasound imaging device, a fluoroscopy imaging device, a magnetic resonance imaging (MRI) device, a single photon emission computed tomography (SPECT) device, a positron emission tomography (PET) device, an X-ray imaging device, or the like, or any combination thereof. For illustration purposes, the present disclosure takes a CT device as an exemplary imaging component 113. This is not intended to be limiting.

In some embodiments, the imaging component 113 may include an imaging radiation source 115, a detector 112, a gantry 111, or the like. The imaging radiation source 115 and the detector 112 may be mounted on the gantry 111. The imaging radiation source 115 may emit radioactive rays to the subject. The detector 112 may detect radiation events (e.g., x-ray photons, gamma-ray photons) emitted from the imaging region of the imaging component 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment component 116 may be configured to deliver a radiotherapy treatment to the subject. The treatment component 116 may include a treatment radiation source 117, a gantry 118, and a collimator 119. The treatment radiation source 117 may be configured to emit treatment radiations towards the subject. In some embodiments, the treatment radiation source 117 may include a linear accelerator (LINAC). The collimator 119 may be configured to control the shape of the treatment radiations generated by the treatment radiation source 117.

In some embodiments, the imaging component 113 may be spaced by a distance from the treatment component 116. In some embodiments, the gantry 111 of the imaging component 113 and the gantry 118 of the treatment component 116 may share an axis of rotation. The subject may be positioned in different positions on the table 114 for imaging and treatment. In some embodiments, the imaging radiation source 115 and the treatment radiation source 117 may be integrated as one radiation source to image and/or treat the subject. In some embodiments, the imaging component 113 and the treatment component 116 may share a same gantry. For example, the treatment radiation source 117 may be mounted on the gantry 111 of the imaging component 113. A subject may be placed on the table 114 for treatment and/or imaging.

In some embodiments, the table 114 may be movable between the treatment component 116 and the imaging component 113 along a certain direction (e.g., a Y-axis direction of a coordinate system 160 as shown in FIG. 1). The table 114 may include a positioning line 170 that extends along the certain direction. The positioning line 170 may have a specific shape, such as an N-shape, an S-shape, a V-shape, so that the positioning line 170 with a positioning feature. The positioning line 170 with the positioning feature may be used to determine a moving path of the table 114. More descriptions regarding the table 114 and/or positioning line 170 may be found elsewhere in the present disclosure. See, e.g., FIGS. 4A to 8 and relevant descriptions thereof.

The network 120 may include any suitable network that can facilitate the exchange of information and/or data for the RT system 100. In some embodiments, one or more components of the RT system 100 (e.g., the radiation delivery device 110, the terminal 130, the processing device 140, the storage device 150, etc.) may communicate information and/or data with one or more other components of the RT system 100 via the network 120. For example, the processing device 140 may obtain image data from the radiation delivery device 110 via the network 120. As another example, the processing device 140 may obtain user instructions from the terminal 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
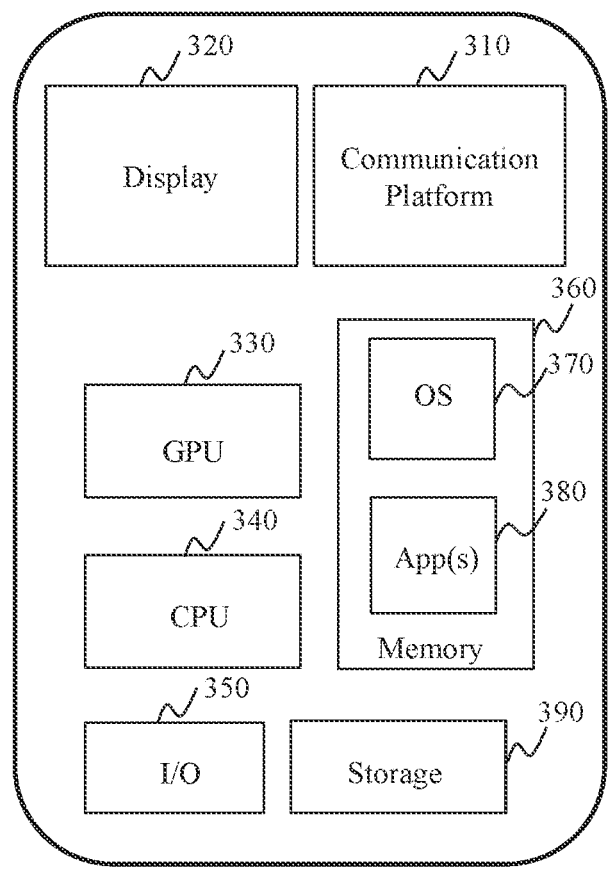
FIG. 3 is a schematic diagram illustrating hardware and/or software components of an exemplary mobile device according to some embodiments of the present disclosure.

The terminal 130 may enable user interaction between a user and the RT system 100. In some embodiments, the terminal 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof.

In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal 130 may be part of the processing device 140.

The processing device 140 may process information obtained from the radiation delivery device 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information stored in the radiation delivery device 110, the terminal 130, and/or the storage device 150 via the network 120. As another example, the processing device 140 may be directly connected to the radiation delivery device 110, the terminal 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the RT system 100 (e.g., the processing device 140, the terminal 130). One or more components of the RT system 100 may access the data and/or instructions stored in the storage device 150 via the network 120. In some embodiments, the storage device 150 may be directly connected to or communicate with one or more other components of the RT system 100 (e.g., the processing device 140, the terminal 130). In some embodiments, the storage device 150 may be part of the processing device 140.

For illustration purposes, a coordinate system 160 including an X-axis, a Y-axis, and a Z-axis is provided in FIG. 1. The X-axis and the Y-axis shown in FIG. 1 may be horizontal, and the Z-axis may be vertical. As illustrated, the positive X direction along the X-axis may be from the left side to the right side of the table 114 seen from the direction facing the front of the radiation delivery device 110; the positive Y direction along the Y-axis shown in FIG. 1 may be from the end to the head of the table 114; the positive Z direction along the Z-axis shown in FIG. 1 may be from the lower part to the upper part of the gantry 118. The origin of the coordinate system 160 may be located at any suitable position. For example, the origin may be located at the isocenter of the LINAC of the treatment component 116, and the coordinate system 160 may be referred to as an RT coordinate system. As another example, the imaging component 113 may be a CT device. The origin of the coordinate system 160 may be located at the rotation center of the gantry 111 of the CT device, and the coordinate system 160 may be referred to as a CT coordinate system. For the convenience of descriptions, coordinates of an entity along an X-axis, a Y-axis, and a Z-axis in a coordinate system are also referred to as an X-coordinate, a Y-coordinate, and Z-coordinate of the entity in the coordinate system, respectively.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. Additionally or alternatively, two or more components of the RT system 100 may be integrated into a single component. A component of the RT system 100 may be implemented on two or more sub-components. In some embodiments, the coordinate system 160 in FIG. 1 is an exemplary coordinate system for illustration purposes and may be modified. For example, the coordinate system 160 may only include two axes (e.g., the X-axis and the Y-axis). In addition, although the following descriptions discusses through various examples to determine a position of an entity by determining a coordinate of an entity in a certain coordinate system, it should be understood that the position of the entity may be determined by determining a coordinate in another coordinate system (e.g., a coordinate system that has a known transformation relationship with the certain coordinate system).

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the radiation delivery device 110, the terminal 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the RT system 100. In some embodiments, the storage 220 may include amass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute to check errors in replanning.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the radiation delivery device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, a terminal 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
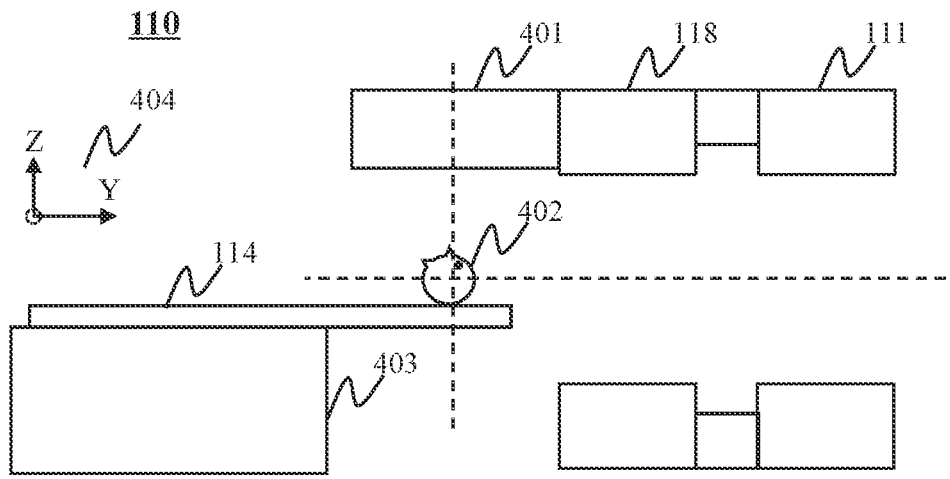
FIGS. 4A and 4B are schematic diagrams illustrating an exemplary radiation delivery device according to some embodiments of the present disclosure.
Figure 4B:
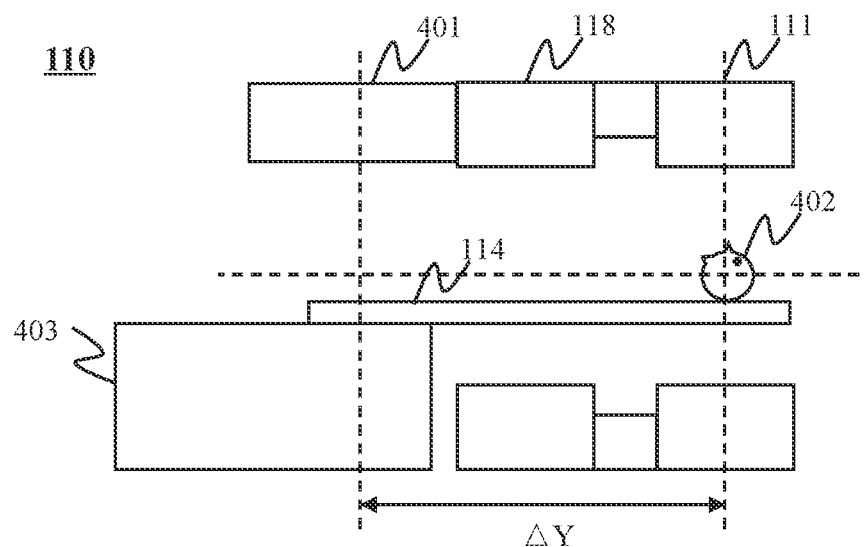

FIGS. 4A and 4B are schematic diagrams illustrating an exemplary radiation delivery device 110 according to some embodiments of the present disclosure. The radiation delivery device 110 may include a treatment component, an imaging component (e.g., a CT device), a table 114, and a table base 403. The treatment component may include a treatment head 401 and a gantry 118. In some embodiments, the treatment head may include a LINAC, a treatment radiation source, a collimator, or the like, or any combination thereof. The imaging component may include a gantry 111, an X-ray source, a detector, or the like, or any combination thereof. The table base 403 may be configured to support the table 114.

In some embodiments, a subject may be placed on the table 114 for treatment and/or imaging. The subject may include any biological subject and/or a non-biological subject. Exemplary biological subject may include a human being, an animal, a plant, or a portion thereof (e.g., a cell, a tissue, an organ, etc.). In some embodiments, the subject may include a region of interest (ROI) 402. The ROI 402 may include a region of the subject including at least part of malignant tissue (e.g., a tumor, a cancer-ridden organ, or a non-cancerous target of radiation therapy) and/or other tissue (e.g., a tissue surrounding the malignant tissue). For example, the ROI 402 may include a target and/or one or more organs-at-risk (OAR). A target may refer to a certain anatomical structure that needs to be tracked and/or monitored during a radiotherapy treatment. For example, the target may be a tumor, an organ with a tumor, a tissue with a tumor, or any combination thereof, that needs to be treated by radiations. An OAR may include an organ (or a portion thereof) and/or a tissue that are close to the target and not indented to be subjected to radiation but under the risk of radiation damage due to its proximity to the target.

In some embodiments, the table 114 may be movable between the treatment component and the imaging component of the radiation delivery device 110 along a Y-axis direction in a coordinate system 404 as illustrated in FIG. 4A, so as to move the subject to different positions. For example, the table 114 may move between a position (denoted as A) as shown in FIG. 4A and a position (denoted as B) as shown in FIG. 4B along the Y-axis. When the table 114 locates at the position A as shown in FIG. 4A, the subject may be located at a first position with respect to the treatment component. The first position may be closer to the treatment component and away from the imaging component, for example, under the treatment head 401 of the treatment component. In some embodiments, the subject may be placed at the first position according to, for example, one or more markers placed on or implanted within the body of the subject, such that the ROI 402 (e.g., an isocenter of a target) may be located at or near the isocenter of the treatment component. In some embodiments, the first position may be also referred to as a set-up position. When the table 114 locates at the position B as shown in FIG. 4B, the subject may be located at a second position with respect to the imaging component. The second position may be closer to the imaging component or faraway from the treatment component. In some embodiments, the subject may be imaged by the imaging component at the second position. Additionally or alternatively, the ROI 402 may be located at or near the second position during the imaging. In some embodiments, the first position may be also referred to as an imaging position.

The coordinate system 404 may be a similar coordinate system as the reference coordinate system 160 as described in connection with FIG. 1. The coordinate system 404 may include the Y-axis, a Z-axis, and an X-axis (which is perpendicular to the plane formed by the Y-axis and the Z-axis and not shown in FIG. 4A). In some embodiments, the origin of the coordinate system 404 may be located at any suitable position. For example, the origin of the coordinate system 404 may be coincident with a mid-point of the head of the table 114 (e.g., the left side of the table as illustrated in FIG. 4A) when the subject is positioned at the first position by the table 114 as shown in FIG. 4A. In some embodiments, the first position and the second position may be represented as a coordinate in the coordinate system 404, respectively. In some embodiments, the coordinate system 404 may also be referred to as a fixed coordinate system with respect to the radiation delivery device 110. A coordinate of an entity in the coordinate system 404 may represent a position of the entity relative to the radiation delivery device 110.

In some embodiments, the radiation delivery device 110 may be used to deliver a radiotherapy treatment to the subject. Conventionally, before the subject begins to receive the radiotherapy treatment (e.g., days or weeks before the treatment commences), a second image (e.g., a CT image) of the subject may be acquired using the imaging device of the radiation delivery device 110. As used herein, a second image may refer to an image according to which a treatment plan for the subject is made. In some embodiments, the second image may be also referred to as a planning image. The treatment plan may describe how the radiotherapy treatment is planned to be performed on the subject, more specifically, how one or more beams are delivered to the ROI 402 of the subject during each treatment fraction over the course of treatment lasting a certain period of time, e.g., days. For example, the treatment plan may provide a total dose (e.g., 0.1 Gy, 10 Gy, 50 Gy, 100 Gy, etc.) and a dose distribution in the ROI 402.

The treatment plan may be delivered to the subject during several treatment fractions, spread over a treatment period of multiple days (e.g., 2 to 5 weeks). However, during the treatment period, an anatomical change (e.g., weight loss, growth, shrinkage, or disappearance of a tumor, the appearance of a new tumor, etc.) may take place within the subject. The size and/or position of a certain organ may change between the time of planning and the time of a treatment fraction. Therefore, every time the subject comes for a treatment fraction, to ensure accurate positioning of the subject for the execution of the specific treatment fraction, the subject may be scanned for generating a first image. The first image may refer to an image of the subject captured during the treatment procedure, for example, right before (e.g., minutes or hours before) the current treatment fraction starts or during the current treatment fraction. The anatomical change of the subject may be identified by comparing the second image and the first image. In some embodiments, the first image may be also referred to as a treatment image. In some embodiments, the second image and the first image may need to be registered so that they may be represented in a common coordinate system. Then, a comparison between the registered second image and the registered first image may be performed so as to determine the anatomical change.

Normally, before the current fraction, the subject may be positioned at a first position as illustrated in FIG. 4A, and be moved to a planned second position via the table 114 as illustrated in FIG. 4B. For example, the table 114 may receive an instruction to move along a planned moving path to reach the planned second position, wherein the planned moving path may be parallel with the Y-axis direction and extend for a specific distance ΔY along the Y-axis direction as illustrated in FIG. 4B. However, due to operation error, the table 114 may move along a moving path different from the planned moving path and reach a second position that is different from the planned second position. For example, the actual moving path of the table 114 may have an angle with the Y-axis direction, which may result in a deviation between the actual second position and the planned second position along the X-axis direction. Merely by way of example, the angle between the actual moving path of the table 114 and the Y-axis direction may be denoted as A (e.g., 0.1 degrees), and a distance of the actual moving path along the Y-axis direction may be denoted as D (e.g., 2100 mm). The deviation (denoted as $D_x$) between the actual second position and the planned second position along the X-axis direction may be determined according to a function $$D_x = D \times \tan\left(A \times \frac{\pi}{180}\right).$$

As another example, the actual moving distance of the table 114 along the Y-axis direction may be smaller than or greater than the specific distance ΔY, which may result in a deviation between the actual second position and the planned second position along the Y-axis direction. As yet another example, due to deformation and/or displacement of the table 114, the actual second position may have a deviation with respect to the planned second position along the Z-axis direction.

As aforementioned, the second image and first image may need to be registered to a common coordinate system so as to identify the anatomical change. The relative position of the actual second position to the first position may need to be determined, so that the first image may be transformed to the common coordinate system accurately. Thus, it is desirable to provide effective mechanisms to determine the relative position, thereby improving the precision of the registration between the second image and the first image, which may in turn improve the treatment reliability and effect. In some embodiments, the table 114 may include a positioning line (e.g., a positioning line 170) having a positioning feature. The relative position may be determined based on the positioning feature of the positioning line. More descriptions regarding the positioning line and the determination of the relative position may be found elsewhere in the present disclosure. See, e.g., FIGS. 5A to 8 and relevant descriptions thereof.

Figure 5A:
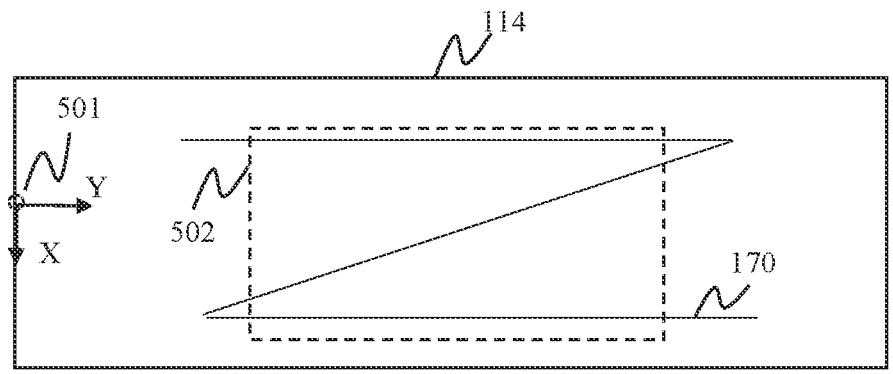
FIGS. 5A to 5C are schematic diagrams of an exemplary table according to some embodiments of the present disclosure.
Figure 5B:
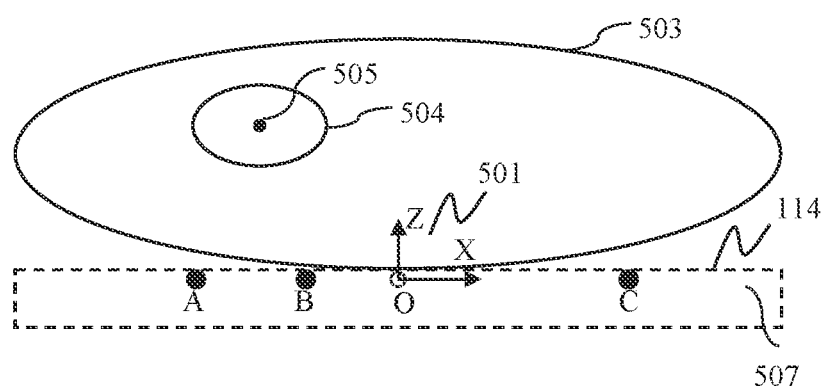
Figure 5C:
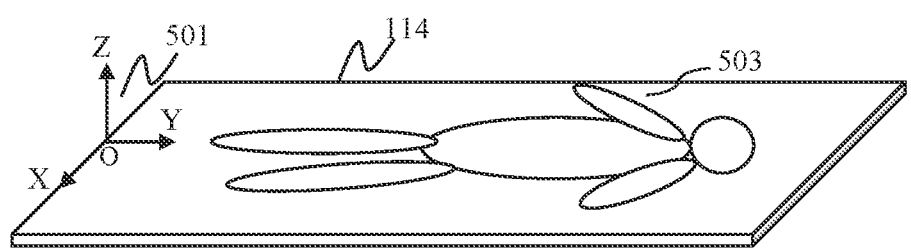

FIGS. 5A to 5C are schematic diagrams of an exemplary table 114 according to some embodiments of the present disclosure. FIG. 5A illustrates a top view of the table 114. FIGS. 5B and 5C illustrate a section view and a perspective view of the table 114 with a patient 503 lying on the table 114. The table 114 may be a component of a radiation delivery device (e.g., the radiation delivery device 110) that includes an imaging device and a treatment component. The radiation delivery device may be configured to treat and/or image the patient 503.

As shown in FIG. 5B, the patient 503 includes an ROI 504 (e.g., a tumor and/or an OAR) with an isocenter 505. In some embodiments, the isocenter 505 of the ROI 504 may be determined by a computing device (e.g., the computing device 200 as illustrated in FIG. 2) based on an image analysis technique and/or a user input (for example, a positioning parameter provided by a user). Alternatively, the isocenter 505 may be marked by a user (e.g., a doctor) via a terminal device (e.g., the terminal 130).

For illustration purposes, a coordinate system 501 is provided in FIGS. 5A to 5C. The coordinate system 501 may be similar to the coordinate system 160 as described elsewhere in this disclosure (e.g., FIG. 1 and the relevant descriptions). The coordinate system 501 may include an X-axis, a Y-axis, and a Z-axis. In treatment and/or imaging, the patient 503 may lie on the table 114 along the Y-axis direction as shown in FIG. 5C. The table 114 may be configured to move between the imaging component and the treatment component along the Y-axis direction to position the patient 503 to a certain position (e.g., a position for treatment or a position for imaging). The origin of the coordinate system 501 is located at any position, for example, a mid-point of the head of the table 114 (e.g., the left side of the table 114 in FIG. 5A). Optionally, the origin of the coordinate system 501 may move with the movement of the table 114. In some embodiments, the coordinate system 501 may also be referred to as a coordinate system with respect to the table 114. A coordinate of an entity in the coordinate system 501 may represent a position of the entity relative to the table 114.

As shown in FIG. 5A, the table 114 may include a positioning line 170 extending along the Y-axis direction. When the table 114 moves along the Y-axis direction, the positioning line 170 may be used to determine a moving trajectory (e.g., a moving direction and/or moving distance) of the table 114. In some embodiments, the positioning line 170 may be mounted on a surface of the table 114 on which the patient 503 lies as illustrated in FIG. 5A via any mounting mechanism, such as glue, adhesive, or the like. Alternatively, the positioning line 170 may be mounted within the table 114. In some embodiments, the density of the positioning line 170 may be different from the density of the table 114, so that the positioning line 170 may be distinguished from the table 114 in an image including the positioning line 170 (or a portion thereof) and the table 114 (or a portion thereof). In some embodiments, the material of the positioning line 170 may be associated with the type of the imaging component of the radiation delivery device. For example, if the imaging component is a CT device, the positioning line 170 may include metal, for example, metal with a low density (e.g., a density lower than a threshold density) such as copper, iron, aluminum, or the like, or any combination thereof. As another example, if the imaging component is an MRI device, the positioning line 170 may include oil.

The positioning line 170 may have any suitable shape and/or size. In some embodiments, different portions of the positioning line 170 may have a uniform diameter. Optionally, the diameter of the positioning line 170 may be within a predetermined range, so that it may be able to be identified by the imaging component. For example, the diameter of the positioning line 170 may range from 0.2 millimeters (mm) to 1 mm, 0.5 mm to 1 mm, 1 mm to 2 mm, 3 mm to 5 mm, or the like. In some embodiments, the diameter of the positioning line 170 may be equal to 0.5 mm, 1 mm, 2 mm, 3 mm, 4 mm, or the like. In some embodiments, the positioning line 170 may cover a field of view (FOV) of the imaging component (e.g., an FOV as indicated by a dotted box 502 in FIG. 5A). As used herein, "cover an FOV" may refer to that a length of the positioning line 170 along the Y-axis direction in the coordinate system 501 is equal to or greater than a length of the FOV along the Y-axis direction. For example, if the length of the FOV along the Y-axis direction is 900 mm, the length of the positioning line 170 along the Y-axis direction may be equal to any value greater than 900 mm, for example, 1000 mm, 1100 mm, 1200 mm, 1500 mm, and so on.

In some embodiments, the positioning line 170 may have a specific shape, such that that the positioning line 170 may have a positioning feature. The positioning feature may have a plurality of unique feature values, each of which may correspond to a distinctive cross section of the table 114. That is, each of the plurality of unique feature values may exclusively correspond to a distinctive cross section of the table 114. As used herein, across section of the table 114 may refer to across section that is perpendicular to the Y-axis direction and a surface of the table 114 on which the patient 503 lies. For illustration purposes, a positioning line 170 having an N-shape as shown in FIG. 5A is taken as an example hereinafter. It should be understood that this is not intended to limit the scope of the present disclosure. The positioning line 170 may have any other shape that provides a positioning line 170 with a positioning feature, for example, an A-shape, an S-shape, a V-shape, a W-shape, an irregular shape, or the like.

As shown in FIG. 5B, for the positioning line 170 with an N-shape, a cross section 507 of the table 114 includes points A, B, and C of the positioning line 170. The point B is located between the points A and C. In some embodiments, the points A, B, and C may also be referred to as a first point, a second point, and a third point of the positioning line 170 at the cross section 507, respectively. Exemplary positioning features of the positioning line 170 may include the coordinates (e.g., X-coordinates in the coordinate system 501) of A and B in combination, the coordinates of B and C in combination, the coordinates of A, B, and C in combination, a distance between the points A and B (represented as |AB|), a distance between the points B and C (represented as |BC|), a ratio of |AB| to |BC|, a ratio of |CB| to |AB|, a difference between |AB| and |BC|, or the like, or any combination thereof. Taking |AB| as an instance, each cross section of the table 114 may have a distinctive distance between a point A and a point B in the cross section, i.e., correspond to a distinctive feature value of the positioning feature. Thus, a value of the distance |AB| may correspond to and be used to identify a unique cross section of the table 114. As another example, each cross section of the table 114 may have a distinctive value of $$\frac{|AB|}{|BC|}.$$

The value of $$\frac{|AB|}{|BC|}$$

may be used to identify a unit cross section of the table 114. Merely by way of example, a value of $$\frac{|AB|}{|BC|}$$

in a cross section is equal to 0.9 and a value of $$\frac{|AB|}{|BC|}$$

in another cross section is equal to 0.1. The cross section may be closer to the left side of the table 114 in FIG. 5A, and the other cross section may be closer to the right side of the table 114 in FIG. 5A. However, in some embodiments, neither the distance between A and C nor the coordinates of A and C in combination can be used as the positioning features of the positioning line 170, since they both do not uniquely correspond to a single cross section of table 114.

In some embodiments, a cross section corresponding to a specific value of the positioning feature may be represented by, for example, a coordinate of a point on the cross section in a coordinate system. For example, the cross section may be represented by a Y-coordinate of a point on the cross section in the coordinate system 501, which represents a relative distance between the cross section and the head of the table 114. As another example, the cross section may be represented by a Y-coordinate in a coordinate system with respect to the radiation delivery device (e.g., the coordinate system 404 as described in FIGS. 4A and 4B).

It should be noted that examples illustrated in FIG. 4A to 5C and the descriptions thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The shape, size, and/or position of a component in FIGS. 4A to 5C are illustrative and may be modified. Additionally or alternatively, the coordinate systems 404 and 501 exemplified above are provided for illustration purposes and not intended to be limiting. Merely by way of example, the origin of the coordinate system 501 may be located at a point other than the mid-point of the head of the table 114, such as a mid-point of the end of the table 114.

Figure 6:
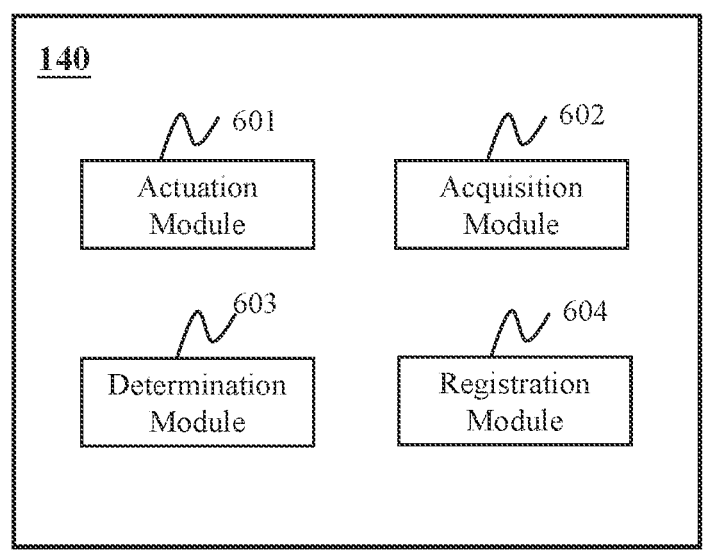
FIG. 6 is a block diagram illustrating an exemplary processing device according to some embodiments of the present disclosure.

FIG. 6 is a block diagram illustrating an exemplary processing device 140 according to some embodiments of the present disclosure. The processing device 140 may process positioning information in a radiotherapy treatment on a subject. In some embodiments, a radiation delivery device (e.g., the radiation delivery device 110) may be used to perform the radiotherapy treatment. The radiation delivery device may include a treatment component (e.g., the treatment component 116), an imaging component (e.g., the second position 113), and a table (e.g., the table 114) including a positioning line (e.g., the positioning line 170)

that extends along a certain direction. As shown in FIG. 6, the processing device 140 may include an actuation module 601, an acquisition module 602, a determination module 603, and a registration module 604.

The actuation module 601 may be configured to control the table of the radiation delivery device. For example, the actuation module 601 may actuate the table to move the subject from a first position with respect to the treatment component to a second position with respect to the imaging component. The second position may refer to a position at which the subject may be imaged for generating a first image by the imaging component. More descriptions regarding the actuation of the table may be found elsewhere in the present disclosure. See, e.g., operation 701 in FIG. 7 relevant descriptions thereof.

The acquisition module 602 may be configured to acquire information relating to the RT system 100. For example, the acquisition module 602 may acquire a first image (or referred to as a first image) including the subject and at least a portion the positioning line. The first image may be acquired using the imaging component when the subject is located at the second position with respect to the imaging component. As another example, the acquisition module 602 may acquire a second image (or referred to as a second image) of the subject. The second image may be captured by the imaging component of the radiation delivery device (or another imaging device) prior to the first image, for example, before the subject begins to receive the radiotherapy treatment (e.g., days or weeks before the radiotherapy treatment commences). More descriptions regarding the acquisition of the first and first images may be found elsewhere in the present disclosure. See, e.g., operations 702 and 704 in FIG. 7 and relevant descriptions thereof.

The determination module 603 may be configured to determine a relative position of the second position to the first position based on the first image and the positioning feature of the positioning line. In some embodiments, the relative position may include a first distance between the second position and the first position along a Y-axis direction in a certain coordinate system and/or a second distance between the second position and the first position along an X-axis direction in the certain coordinate system. More descriptions regarding the determination of the relative position may be found elsewhere in the present disclosure. See, e.g., operation 703 in FIG. 7 and relevant descriptions thereof.

The registration module 604 may be configured to perform image registration. For example, the registration module 604 may register the first image and the second image based on the relative position of the second position to the first position. In some embodiments, the registration between the second image and the first image may be performed with respect to a coordinate system so that they are both represented in the coordinate system. More descriptions regarding the registration of the first image and the second image may be found elsewhere in the present disclosure. See, e.g., operation 705 in FIG. 7 relevant descriptions thereof.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. Additionally or alternatively, two or more modules may be integrated into a single module and/or a module may be divided into two or more units. However, those variations and modifications also fall within the scope of the present disclosure.

FIG. 7 is a flowchart illustrating an exemplary process for registering a second image with a first image according to some embodiments of the present disclosure. In some embodiments, process 700 may be executed by the RT system 100. For example, the process 700 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 6) may execute the set of instructions and may accordingly be directed to perform the process 700.

In some embodiments, a radiation delivery device (e.g., the radiation delivery device 110) may be used to perform a radiotherapy treatment on a subject (e.g., a patient, a portion of the patient, a man-made object, etc.). The radiation delivery device may include a treatment component (e.g., the treatment component 116), an imaging component (e.g., the second position 113), and a table (e.g., the table 114). The subject may be placed on the table, and the table may be is movable between the treatment component and the imaging component along a Y-axis direction in a first coordinate system to move the subject to different positions. The table may include a positioning line that extends along the Y-axis direction and has a positioning feature. The positioning feature of the positioning line may have a plurality of feature values, each of which may correspond to a distinctive cross section of the table. The first coordinate system may be a same or similar coordinate system as the coordinate system 160 or 404 as described elsewhere in this disclosure. For example, the first coordinate system may include an X-axis, the Y-axis, and optionally a Z-axis. The X-axis direction may be parallel with a surface of the table on which the subject lies and perpendicular to the Y-axis. The Z-axis may be perpendicular to a plane formed by the X-axis and the Y-axis. In some embodiments, the Y-axis direction and the X-axis direction may be also referred to as a first direction and a second direction of the first coordinate system, respectively.

As described elsewhere in this disclosure, the radiotherapy treatment may include a plurality of treatment fractions and last for a treatment period of multiple days (e.g., 2 to 5 weeks). As the treatment progresses, an anatomical change may take place within an ROI (e.g., a target and/or an OAR) of the subject during the treatment period. Every time the subject comes for a current treatment fraction, to ensure accurate first positioning of the subject for the execution of the current treatment fraction, the subject may be scanned for generating a first image. In some embodiments, before the first image is acquired during the current treatment fraction, the subject may be placed at a first position via the table. For example, the subject may be placed at a first position adjacent to the treatment component and away from the imaging component as illustrated in FIG. 4A. Optionally, the ROI of the subject may be located at the isocenter of a LINAC of the treatment component when the subject is placed at the first position. In some embodiments, the mid-point of an end of the table (e.g., the head of the table) may be coincident with the origin of the first coordinate system when the subject is placed at the first position.

In 701, the processing device 140 (e.g., the actuation module 601) may actuate the table to move the subject from the first position with respect to the treatment component to a second position with respect to the imaging component.

The second position may refer to a position at which the subject may be imaged for generating the first image by the imaging component. In some embodiments, the table may move along a moving path to reach to the second position. The moving path may be parallel with or substantially parallel with the Y-axis direction in the first coordinate system. As aforementioned, in some occasions, the moving path of the table may be different from a planned moving path and the second position may be different from a planned second position. The deviation between the second position and the planned second position may be caused by an operation error of the table.

In 702, the processing device 140 (e.g., the acquisition module 602) may acquire the first image including the subject and at least a portion the positioning line using the imaging component. The subject may be located at the second position during the acquisition of the first image.

For example, the processing device 140 may direct the imaging component to perform a scan on the subject to acquire scan data of the subject. The FOV of the imaging component during the scan may cover the subject and the at least a portion of the positioning line. The processing device 140 may reconstruct the first image based on the scan data. Alternatively, another device (e.g., the radiation delivery device 110 or another computing device) may reconstruct the first image and transmit the first image to the processing device 140 via the network 120. Alternatively, the first image may be reconstructed by another device and stored in a storage device (e.g., the storage device 150, the storage 220, an external source). The processing device 140 may retrieve the first image from the storage device.

In 703, the processing device 140 (e.g., the determination module 603) may determine a relative position of the second position to the first position based on the first image and the positioning feature of the positioning line.

In some embodiments, the relative position of the second position to the first position may include a first distance between the second position and the first position along the Y-axis direction in the first coordinate system and/or a second distance between the second position and the first position along the X-axis direction in the first coordinate system. In some embodiments, the processing device 140 may determine the relative position by performing one or more operations of process 800 as described in connection with FIG. 8.

In 704, the processing device 140 (e.g., the acquisition module 602) may obtain a second image of the subject.

The second image may be captured by the imaging component of the radiation delivery device (or another imaging device) prior to the first image, for example, before the subject begins to receive the radiotherapy treatment (e.g., days or weeks before the radiotherapy treatment commences). In some embodiments, the second image may be obtained from a storage device (e.g., the storage device 150, the storage 220, or the storage 390) or an external resource that stores the second image.

In 705, the processing device 140 (e.g., the registration module 604) may register the first image and the second image based on the relative position of the second position to the first position.

In some embodiments, the registration between the second image and the first image may be performed with respect to a second coordinate system so that they are both represented in the second coordinate system. The second coordinate system may be any suitable coordinate system. For example, the second coordinate system may be a same or similar coordinate system as the coordinate system 160 or 404 as described elsewhere in this disclosure. The second coordinate system may be same as or different from the first coordinate system. In some embodiments, the second coordinate system may be an RT coordinate system or a CT coordinate system as described in connection with FIG. 1.

In some embodiments, during the registration, the processing device 140 may transform the second image into a transformed second image in the second coordinate system. For example, if originally the second image is represented in a coordinate system other than the second coordinate system, the processing device 140 may transform a coordinate of each pixel (or voxel) in the second image to a coordinate in the second coordinate system. As another example, if originally the second image is represented in the second coordinate system, the processing device 140 may designate the second image as the transformed second image.

The processing device 140 may also transform the first image into a transformed first image in the second coordinate system based on the relative position of the second position to the first position. In some embodiments, as described in connection with operation 703, the relative position may include a first distance between the second position and the first position along the Y-axis direction and/or a second distance between the second position and the first position along the X-axis direction in the first coordinate system. The first distance and/or the second distance may be taken into consideration in the transformation of the first image. Merely by way of example, the second coordinate system may be the RT coordinate system whose origin is located at the LINAC isocenter of the treatment component. In the transformation of the first image, a coordinate of each pixel (or voxel) in the first image may be moved for the first distance along a direction opposite to the Y-axis direction and/or moved for the second distance along a direction opposite to the X-axis direction. For example, according to the relative position, the subject is moved for the first distance along a positive Y-axis direction and for the second distance along a positive X-axis direction of the first coordinate system to reach the second position. The transformed first image may be obtained by moving a coordinate of each pixel (or voxel) in the first image for the first distance along a negative Y-axis direction and for the second distance along a negative X-axis direction. In this way, a deviation of the second position with respect to the planned second position due to operation error may be eliminated or reduced.

Optionally, the processing device 140 may align the transformed second image with the transformed first image to generate an aligned second image and an aligned first image. In some embodiments, the transformed second image and the transformed first image may be aligned to share a common isocenter. For example, the isocenter of the transformed second image (e.g., an isocenter of a target in the transformed second image) and the isocenter of the transformed first image (e.g., an isocenter of the target in the transformed first image) may be coincident so that the transformed second image and the transformed first image share a common isocenter. Optionally, the common isocenter may be coincident with the LINAC isocenter of the treatment component.

The processing device 140 may register the aligned first image with the aligned second image. The registration may be performed based on any suitable image registration techniques including, for example, a voxel-based registration technique, a landmark-based registration technique, a segmentation-based registration technique, or the like, or a combination thereof. In some embodiments, the registration between the aligned second image and the aligned first image may include a rigid registration. In some embodiments, a registration matrix between the aligned second image and the aligned first image may be determined in the registration. The registration matrix may represent a transformation relationship between the aligned first image and the aligned second image. For example, if a voxel of a certain physical point in the aligned second image has a coordinate C in the second coordinate system and a voxel of the same physical point in the first image has a coordinate D in the second coordinate system, the registration matrix may record a transformation relationship between the coordinates C and D.

In some embodiments, the processing device 140 may determine a first position for the execution of the current treatment fraction based on the registration result. The subject may be placed to the first position for the execution of the current treatment fraction via the table. Additionally or alternatively, the processing device 140 may determine whether the treatment plan needs to be modified based on the registration result. For example, the processing device 140 may compare the ROI in the registered second image and the ROI in the registered first image. If the comparison result indicates that the amount of change of the ROI exceeds a threshold, the original treatment plan may need to be modified in order to reduce toxicity to the portions of the subject by unintended radiation and improve targeting of the target and overall outcome of the treatment. Optionally, the modified treatment plan may be performed on the subject in the current treatment fraction or a subsequent treatment fraction. In some embodiments, the amount of the change of the ROI may be measured by a change in one or more of features of the ROI including, e.g., the size, the position, the volume, the shape, or the like, of the ROI.

According to some embodiments of the present disclosure, the registration between the second image and the first image may be performed according to the relative position of the second position to the first position determined based on the positioning line. Compared with performing the registration based on the planned moving path, this may eliminate or reduce the influence of the operation error of the table and improve the accuracy and/or reliability of the registration, which may further improve the precision of treatment delivery and/or reduce or avoid unnecessary damages to the subject caused by inaccurate radiation delivery to the subject.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 700 may be accomplished with one or more additional operations not described and/or without one or more of the operations discussed above. For example, operations 704 and 705 may be omitted. Additionally, the order of the process 700 may not be intended to be limiting. For example, the operation 704 may be performed before operation 701.

FIG. 8 is a flowchart illustrating an exemplary process for determining a relative position of a second position to a first position according to some embodiments of the present disclosure. In some embodiments, process 800 may be executed by the RT system 100. For example, the process 800 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 6) may execute the set of instructions and may accordingly be directed to perform the process 800. In some embodiments, one or more operations of the process 800 may be performed to achieve at least part of operation 703 as described in connection with FIG. 7.

In 801, the processing device 140 (e.g., the determination module 603) may determine a third position of a first cross section of the table in the first coordinate system. The first cross section may pass through an isocenter of the treatment component when the subject locates at the first position.

The isocenter of the treatment component may refer to the LINAC isocenter of the treatment component. The third position of the first cross section may include a Y-coordinate of the first cross section in the first coordinate system. The Y-coordinate may be a Y-coordinate of any point on the first cross section in the first coordinate system. Because the first cross section may be perpendicular to the Y-axis direction, the points on the first cross section may have a same Y-coordinate along the Y-axis. Additionally or alternatively, the third position of the first cross section may include an X-coordinate of at least one point of the positioning line at the first cross section in the first coordinate system. For illustration purposes, it is assumed that the positioning line has an N-shape as illustrated in FIG. 5A, and the first cross section has points $A_0$, $B_0$, and $C_0$ of the positioning line. The point $B_0$ may be located between point $A_0$ and $C_0$. The Y-coordinates the points $A_0$, $B_0$, and $C_0$ in the first coordinate system may be represented as $Y_{A0}$, $Y_{B0}$, and $Y_{C0}$, respectively. The X-coordinates of the points $A_0$, $B_0$, and $C_0$ in the first coordinate system may be represented as $X_{A0}$, $X_{B0}$, and $X_{C0}$, respectively. The third position of the first cross section may be represented by any one of $Y_{A0}$, $Y_{B0}$, and $Y_{C0}$ and/or one or more of $X_{A0}$, $X_{B0}$, and $X_{C0}$.

In some embodiments, an encoder may be used to detect the position of the table when the subject locates at the first position. For example, the encoder may detect a Y-coordinate of the table (e.g., the head or the end of the table) in the first coordinate system. The Y-coordinate of the first cross section in the first coordinate system may be determined based on the Y-coordinate of the head (or the end) of the table and the position of the first cross section relative to the table. The position of the first cross section relative to the table may be represented by, for example, a distance the first cross section to a reference location (e.g., the head or end) of the table and/or a Y-coordinate of the cross section in a coordinate system with respect to the table (e.g., the coordinate system 501 as shown in FIGS. 5A to 5C).

In some embodiments, the X-coordinate of a point on the first cross section in the first coordinate system may be determined based on a first lookup table that stores X-coordinates of point(s) in a plurality of cross sections of the table in the first coordinate system (or another coordinate system that has a known transformation relationship with the first coordinate system). For example, the coordinates $X_{A0}$, $X_{B0}$, and $X_{C0}$ may be determined based on the position of the first cross section relative to the table by looking up the first look-up table.

In 802, the processing device 140 (e.g., the determination module 603) may determine a feature value of the positioning feature corresponding to the first cross section of the table.

In some embodiments, each cross section of the table may include a first point, a second point, and a third point of the N-shape positioning line at the cross section, wherein the second point may be located between the first and third points. The positioning feature may include, for example, a first distance between the first and second points, a second distance between the second and third points, a ratio of the first distance to the second distance, or the like. The processing device 140 may determine the feature value corresponding to the first cross section based on one or more of the X-coordinates $X_{A0}$, $X_{B0}$, and $X_{C0}$. For example, the first distance corresponding to the first cross section may be equal to $|X_{A0}-X_{B0}|$. Alternatively, the processing device 140 may obtain a second lookup table recording feature values of the positioning feature corresponding to a plurality of cross sections of the table. For example, the second lookup table may record a position of each cross section relative to the table and its feature value of the positioning feature. The processing device 140 may determine the feature value corresponding to the first cross section based on the third position of the first cross section relative to the table by looking up the second lookup table.

In some embodiments, the second lookup table and the first lookup table may be a same lookup table or different lookup tables. Merely by way of example, the first and second lookup tables may be a same lookup table recording cross sections at different positions, as well as a corresponding feature value of the cross section and X-coordinates of points of the positioning line on each cross section. For a certain cross section, the processing device 140 may simultaneously determine the corresponding feature value of the cross section and the X-coordinates of points of the positioning line on the certain cross section by looking up the lookup table. In some embodiments, the positioning feature may be coordinates (e.g., X-coordinates) of the first and second points in combination, the coordinates of the second and third points in combination, the coordinates of the first, second, and third points in combination. Operation 802 may be omitted or integrated into 801.

In 803, the processing device 140 (e.g., the determination module 603) may identify, in the first image, a second cross section of the table that matches the first cross section based on the feature value of the positioning feature corresponding to the first cross section.

In some embodiments, the processing device 140 may identify a plurality of cross sections of the table in the first image, and determine their corresponding feature values of the positioning feature based on the first image. The processing device 140 may further determine, among the cross sections of the table in the first image, the second cross section that matches the first cross section. The selected second cross section matching the first cross section may be, for example, a cross section that has a same feature value as the first cross section, a cross section who has a substantially same feature value as the first cross section (e.g., the difference between the feature values of the first and second cross sections being smaller than a threshold), a cross section whose feature value is closest to the feature of the first cross section among the identified cross sections, or the like. Merely by way of example, it is assumed that the positioning feature of the positioning line is the first distance between the first point and the second point in each cross section. The feature value of the positioning feature corresponding to the first cross section may be the distance between $A_0$ and $B_0$. The processing device 140 may determine the first distance corresponding to each identified cross section based on the first image, for example, by determining the first distance in physical space based on a first distance in the first image corresponding to each cross section and an image scale of the first image. The selected second cross section matching the first cross section may include three points $A_1$, $B_1$, and $C_1$ of the positioning line. The point $B_1$ may be located between point $A_1$ and $C_1$. The points $A_1$, $B_1$, and $C_1$ may correspond to the point $A_0$, $B_0$, and $C_0$, respectively. The distance between $A_1$ and $B_1$ may be equal to or substantially equal to the distance between $A_0$ and $B_0$.

In 804, the processing device 140 (e.g., the determination module 603) may determine a fourth position of the second cross section in the first coordinate system based on the first image instead of using the encoder, in order to obviate the errors caused by deflection or inaccurate position of the table.

In some embodiments, similar to the third position of the first cross section, the fourth position of the second cross section may include a Y-coordinate of the second cross section and/or an X-coordinate of at least a point in the second cross section in the first coordinate system. For example, the second cross section matching the first cross section may include points $A_1$, $B_1$, and $C_1$ of the positioning line as described above. The Y-coordinates of the points $A_1$, $B_1$, and $C_1$ in the first coordinate system may be represented as $Y_{A1}$, $Y_{B1}$, and $Y_{C1}$, respectively. The X-coordinates of the points $A_1$, $B_1$, and $C_1$ in the first coordinate system may be represented as $X_{A1}$, $X_{B1}$, and $X_{C1}$, respectively. The fourth position may represent be represented by any one of $Y_{A1}$, $Y_{B1}$, and $Y_{C1}$ and/or one or more of $X_{A1}$, $X_{B1}$, and $X_{C1}$. In some embodiments, if the third position of the first cross section is represented by a coordinate (e.g., the X-coordinate and/or the Y-coordinate) of a specific point of $A_0$, $B_0$, and $C_0$, the fourth position of the second cross section may be represented by a coordinate of a point corresponding to the specific point. Merely by way of example, if the third position is represented by $Y_{A0}$ and $X_{A0}$, the fourth position may be represented by $Y_{A1}$ and $X_{A1}$.

In some embodiments, the fourth position of the second cross section in the first coordinate system may be determined by analyzing the first image. For example, the first image may be represented in a coordinate system with respect to the imaging component (e.g., a CT coordinate system if the imaging component is a CT device). The processing device 140 may determine the fourth position according to the first image and the transformation relationship between the first coordinate system and the coordinate system with respect to the imaging component.

In 805, the processing device 140 (e.g., the determination module 603) may determine the relative position of the second position to the first position based on the third position and the fourth position.

In some embodiments, the relative position may include a first distance between the second position and the first position along the Y-axis direction of the first coordinate system. The first distance may be equal to a difference between the Y-coordinate of the first cross section and the Y-coordinate of the second cross section. For example, if the Y coordinates of the first and second cross sections are 2000 mm and 2500 mm, respectively, the first distance may be equal to 500 mm.

Additionally or alternatively, the relative position may include a second distance between the second position and the first position along the X-axis direction of the first coordinate system. The processing device 140 may determine the second distance based on the X-coordinate of the at least one point of the positioning line at the first cross section and the X-coordinate of the at least one point of the positioning line at the second cross section. For example, the second distance may be equal to any one of $(X_{A0}-X_{A1})$, $(X_B-X_{B1})$, and $(X_0-X_{C1})$. As another example, the second distance may be equal to an average value of at least two of $(X_{A0}-X_{A1})$, $(X_B-X_{B1})$, and $$(X_0 - X_{C1}) \left(\text{e.g., } \frac{(X_{A0} - X_{A1}) + (X_{B0} - X_{B1})}{2}, \frac{(X_{A0} - X_{A1}) + (X_B - X_{B1}) + (X_0 - X_{C1})}{3}\right).$$

In some embodiments, a positive second distance may indicate that the actual moving path of the table has a deviation with respect to the planned moving path along the positive X-axis direction. A negative second distance may indicate that the actual moving path of the table has a deviation with respect to the planned moving path along the negative X-axis direction. In some embodiments, the determined relative position of the second position to the first position may be used in registering the second image and the first image as described in connection with operation 705.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 800 may be accomplished with one or more additional operations not described and/or without one or more of the operations discussed above. In some embodiments, two or more operations may be combined into a single operation. For example, operations 801 and 802 may be combined into a single operation. Additionally or alternatively, operations 803 and 804 may be combined into a single operation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiotherapy system, comprising:
   a treatment component;
   an imaging component;
   a table being movable between the treatment component and the imaging component along a first direction in a first coordinate system, the table having a plurality of cross sections perpendicular to the first direction, the table including a positioning line that extends along the first direction and has a positioning feature, the positioning feature having a plurality of feature values, each feature value corresponding to one of the plurality of cross sections;
   at least one storage device storing a set of instructions for positioning in radiotherapy treatment and a first position; and
   at least one processor configured to communicate with the at least one storage device, wherein when executing the set of instructions, the at least one processor is configured to direct the system to perform operations including:
      actuating the table to move a subject from the first position with respect to the treatment component to a second position with respect to the imaging component, the first position is a position where the subject is located when a first cross section of the table passes through an isocenter of the treatment component;
      acquiring, using the imaging component, a first image including the subject and at least one a portion of the positioning line, the subject being located at the second position during the acquisition of the first image; and
      determining, based on the first image and the positioning feature of the positioning line, a relative position of the second position to the first position.

2. The system of claim 1, wherein to determine a relative position of the second position to the first position, the at least one processor is further configured to direct the system to perform additional operations including:
   determining a third position of a first cross section of the table in the first coordinate system;
   determining a feature value of the positioning feature corresponding to the first cross section of the table;
   identifying, in the first image, based on the feature value of the positioning feature corresponding to the first cross section, a second cross section of the table that matches the first cross section, wherein the second cross section has the same feature value as the first cross section;
   determining a fourth position of the second cross section in the first coordinate system; and
   determining, based on the third position and the fourth position, the relative position of the second position to the first position.

3. The system of claim 2, wherein:
   the third position of the first cross section includes a first coordinate of the first cross section along the first direction,
   the fourth position of the second cross section includes a second coordinate of the second cross section along the first direction,
   the relative position includes a first distance between the second position and the first position along the first direction, and to determine a relative position of the second position to the first position, the at least one processor is further configured to direct the system to perform additional operations including:
   determining, based on the first coordinate and the second coordinate, the first distance.

4. The system of claim 2, wherein:
   the third position of the first cross section includes a third coordinate of at least one point of the positioning line at the first cross section along a second direction, the second direction being parallel with a surface of the table on which the subject lies and perpendicular to the first direction, the fourth position of the second cross section includes a fourth coordinate of at least one point of the positioning line at the second cross section along the second direction, the relative position includes a second distance between the second position and the first position along the second direction, and to determine the relative position of the second position to the first position, the at least one processor is further configured to direct the system to perform additional operations including:

determining, based on the third coordinate and the fourth coordinate, the second distance.

5. The system of claim 2, wherein to determine a feature value of the positioning feature corresponding to the first cross section of the table, the at least one processor is further configured to direct the system to perform additional operations including:

obtaining a lookup table recording feature values of the positioning feature corresponding to the plurality of cross sections of the table; and determining, based on the third position of the first cross section, the feature value of the positioning feature corresponding to the first cross section of the table by looking up the lookup table.

6. The system of claim 1, the at least one processor is further configured to direct the system to perform additional operations including:

obtaining a second image of the subject, the second image being captured prior to the first image; and registering, based on the relative position of the second position to the first position, the first image and the second image with each other.

7. The system of claim 1, wherein:

the positioning line has an N-shape, a cross section of the plurality of cross sections has a first point, a second point, and a third point of the positioning line, the second point being located between the first point and the third point, and the positioning feature includes at least one of a third distance between the first point and the second point, a fourth distance between the second point and the third point, a ratio of the third distance to the fourth distance, a ratio of the fourth distance to the third distance, or a difference between the third distance and the fourth distance.

8. The system of claim 1, wherein the positioning line has at least one of an A-shape, an S-shape, a V-shape, or a W-shape.

9. The system of claim 1, wherein a density of the positioning line is different from a density of the table.

10. The system of claim 1, wherein:

the imaging component is a computed tomography device, and the positioning line includes at least one of copper, iron, or aluminum, or the imaging component is a magnetic resonance imaging device, and the positioning line includes oil.

11. A method for patent positioning implemented on a radiotherapy system, wherein the radiotherapy system comprises:

a treatment component;
an imaging component;
a table being movable between the treatment component and the imaging component along a first direction in a first coordinate system, the table having a plurality of cross sections perpendicular to the first direction, the table including a positioning line that extends along the first direction and has a positioning feature, the positioning feature having a plurality of feature values, each feature value corresponding to one of the plurality of cross sections; and at least one storage device storing a first position, and the method comprises:

actuating the table to move a subject from a first position with respect to the treatment component to a second position with respect to the imaging component, the first position is a position where the subject is located when a first cross section of the table passes through an isocenter of the treatment component;

acquiring, using the imaging component, a first image including the subject and at least one a portion of the positioning line, the subject being located at the second position during the acquisition of the first image; and determining, based on the first image and the positioning feature of the positioning line, a relative position of the second position to the first position.

12. The method of claim 11, wherein the determining a relative position of the second position to the first position comprises:

determining a third position of a first cross section of the table in the first coordinate system;

determining a feature value of the positioning feature corresponding to the first cross section of the table;

identifying, in the first image, based on the feature value of the positioning feature corresponding to the first cross section, a second cross section of the table that matches the first cross section, wherein the second cross section has the same feature value as the first cross section;

determining a fourth position of the second cross section in the first coordinate system; and determining, based on the third position and the fourth position, the relative position of the second position to the first position.

13. The method of claim 12, wherein:

the third position of the first cross section includes a first coordinate of the first cross section along the first direction, the fourth position of the second cross section includes a second coordinate of the second cross section along the first direction, the relative position includes a first distance between the second position and the first position along the first direction, and the determining a relative position of the second position to the first position comprises:

determining, based on the first coordinate and the second coordinate, the first distance.

14. The method of claim 12, wherein:

the third position of the first cross section includes a third coordinate of at least one point of the positioning line at the first cross section along a second direction, the second direction being parallel with a surface of the table on which the subject lies and perpendicular to the first direction, the fourth position of the second cross section includes a fourth coordinate of at least one point of the positioning line at the second cross section along the second direction, the relative position includes a second distance between the second position and the first position along the second direction, and the determining the relative position of the second position to the first position comprises:
determining, based on the third coordinate and the fourth coordinate, the second distance.

15. The method of claim 12, wherein the determining a feature value of the positioning feature corresponding to the first cross section of the table comprises:
obtaining a lookup table recording feature values of the positioning feature corresponding to the plurality of cross sections of the table; and
determining, based on the third position of the first cross section, the feature value of the positioning feature corresponding to the first cross section of the table by looking up the lookup table.

16. The method of claim 11, the method further comprises:
obtaining a second image of the subject, the second image being captured prior to the first image; and
registering, based on the relative position of the second position to the first position, the first image and the second image with each other.

17. The method of claim 11, wherein:
the positioning line has an N-shape, a cross section of the plurality of cross sections has a first point, a second point, and a third point of the positioning line, the second point being located between the first point and the third point, and
the positioning feature includes at least one of a third distance between the first point and the second point, a fourth distance between the second point and the third point, a ratio of the third distance to the fourth distance, a ratio of the fourth distance to the third distance, or a difference between the third distance and the fourth distance.

18. The method of claim 11, wherein a density of the positioning line is different from a density of the table.

19. A non-transitory computer-readable storage medium including a set of instructions for positioning in radiotherapy treatment using a radiotherapy system and a first position, wherein the radiotherapy system comprises:
a treatment component;
an imaging component; and
a table being movable between the treatment component and the imaging component along a first direction in a first coordinate system, the table having a plurality of cross sections perpendicular to the first direction, the table including a positioning line that extends along the first direction and has a positioning feature, the positioning feature having a plurality of feature values, each feature value corresponding to one of the plurality of cross sections, wherein when the set of instructions is executed by at least one processor, the set of instructions direct the at least one processor to effectuate a method, the method comprising:
actuating the table to move a subject from a first position with respect to the treatment component to a second position with respect to the imaging component, the first position is a position where the subject is located when a first cross section of the table passes through an isocenter of the treatment component;
acquiring, using the imaging component, a first image including the subject and at least one a portion of the positioning line, the subject being located at the second position during the acquisition of the first image; and
determining, based on the first image and the positioning feature of the positioning line, a relative position of the second position to the first position.

* * * * *